United States Patent [19]

Simon et al.

[11] Patent Number: 5,671,755
[45] Date of Patent: Sep. 30, 1997

[54] ASSEMBLY AND METHOD FOR CONTROLLING URINARY INCONTINENCE IN HUMANS

[75] Inventors: John Simon, Boston; Paul McLaughlin, Scituate, both of Mass.; Leo Felice, Pascoag, R.I.; Michelle Maxfield-Bahr, Somerville; Sharad Joshi, Watertown, both of Mass.

[73] Assignee: UroMed Corporation, Needham, Mass.

[21] Appl. No.: 267,487

[22] Filed: Jun. 29, 1994

[51] Int. Cl.[6] ............................................. A61F 5/48
[52] U.S. Cl. ............................. 128/885; 128/DIG. 25; 600/29
[58] Field of Search ..................... 128/846, 885, 128/DIG. 25; 600/29–31; 604/11–18, 359, 904

[56] References Cited

U.S. PATENT DOCUMENTS

| | | | |
|---|---|---|---|
| 702,570 | 6/1902 | Lohlein | 604/15 |
| 4,286,596 | 9/1981 | Rubinstein | 604/904 |
| 4,361,150 | 11/1982 | Voss | 604/15 |
| 4,726,805 | 2/1988 | Sanders, III | 604/15 |
| 4,822,332 | 4/1989 | Kajander | 604/16 |
| 5,090,424 | 2/1992 | Simon et al. | 128/885 |
| 5,131,906 | 7/1992 | Chen | 600/29 |
| 5,158,535 | 10/1992 | Paul | 604/904 |
| 5,352,182 | 10/1994 | Kalb et al. | 600/30 |

FOREIGN PATENT DOCUMENTS 0075036  6/1954  Netherlands ........................ 604/904

OTHER PUBLICATIONS

PCT Publication WO 90/04431 of Fusen Chen, published May 3, 1990 (May 3, 1990).

*Primary Examiner*—Michael A. Brown
*Attorney, Agent, or Firm*—Lorusso & Loud

[57] ABSTRACT

There is presented an assembly for prevention of urinary incontinence in humans, the assembly comprising an applicator and an elastomer body. The applicator is adapted to position the elastomer body in the urethra of a female or male and includes a support portion for retaining the elastomer body, and a manipulable portion for positioning the elastomer body in the urethra. There is further presented a method for preventing an unwanted discharge of urine, utilizing the aforesaid assembly.

13 Claims, 10 Drawing Sheets

ASSEMBLY AND METHOD FOR CONTROLLING URINARY INCONTINENCE IN HUMANS

BACKGROUND OF THE INVENTION (1) Field of the Invention

This invention relates to foam or elastomer occlusion devices and is directed more particularly to a disposable body of foam or elastomer material, an applicator for positioning and depositing the body of material in the urethra of a human, and a method for preventing unwanted discharge of urine.

(2) Description of the Prior Art

Flexible urethral plugs for treatment of incontinence are known in the art. In U.S. Pat. No. 5,090,424, issued Feb. 25, 1992 in the names of John G. Simon and James E. Nicholson, there is disclosed a flexible urethral plug having a molded soft inflatable plastic catheter and a transportable fluid disposed in a bellows in communication with the catheter. In use, the fluid, preferably silicon gel, can be moved from the bellows, which remain externally of the urethra, through a check valve, to inflate and distend the catheter within the urethra, bladder neck, or bladder, to block the flow of urine through the urethra. Removal of the device requires a tug on the bellows, which causes the check valve to open, permitting the fluid in the catheter to flow back into the bellows, to reduce the size of the catheter to facilitate withdrawal of the catheter from the urethra.

While the above-described device has proven beneficial, it requires the manufacture and precise placement of the check valve within the device and requires that appropriate fluid be captured within, or injected into, the device. Accordingly, the device is relatively expensive to manufacture and therefore expensive to the patient. There is a need for expandable plugs of the general type described above, but with simple mechanical expansion means, rather than hydraulic expansion means requiring fluid flow and a check valve.

There are a number of sponge-like devices used to prevent involuntary loss of urine. Such devices generally are inserted into the urethra by hand, a sometimes difficult and painful undertaking, and often not done well enough to correctly position the device in the urethra. Other devices, for women, are inserted by hand into the vagina to support the urethra. The latter devices, however, do not consistently prevent involuntary voiding.

There is thus a need for a mechanically expandable plug which may be used in conjunction with an applicator which assures painless ease and accuracy in positioning the plug in the urethra.

SUMMARY OF THE INVENTION

An object of the invention is, therefore, to provide an assembly for the prevention of urinary incontinence in humans, the assembly being expandable to block the urethra, but requiring no fluid and, therefore, no valve within the assembly to effect expansion.

A further object is to provide such an assembly having an appropriately expandable body for effecting blockage of urine, and also having an applicator by which the body may be properly positioned within the urethra.

A still further object of the invention is to provide a method for preventing an unwanted discharge of urine, utilizing the aforesaid assembly.

With the above and other objects in view, as will hereinafter appear, a feature of the present invention is the provision of an assembly for prevention of urinary incontinence in humans, the assembly including an applicator for positioning a foam or elastomer body in a urethra of a female or male. The applicator comprises a support portion for retaining the foam or elastomer body, and a manipulable portion for disengaging the foam body from at least a portion of the applicator. The assembly further includes the foam or elastomer body which comprises a discrete body of foam or elastomer material mounted on the applicator support portion.

In accordance with a further feature of the invention, there is provided an assembly for prevention of urinary incontinence in humans, the assembly including an applicator for positioning a foam body in a urethra of a female or male. The applicator comprises a support portion for retaining the foam or elastomer body, the support portion comprising a tubular shell open at a first end and having a second end closed but slit so as to be adapted to open in response to pressure thereupon internally of the shell, and a manipulable portion comprising a plunger in part disposed in the shell open first end, the plunger being engageable with the foam body at a first end of the plunger and having a head at a second end thereof. The assembly further includes the foam or elastomer body which comprises a discrete elongated body of foam or elastomer material mounted in the shell. The applicator plunger is moveable in the shell to force the foam or elastomer body through the shell second end to disengage the foam or elastomer body from the applicator shell.

In accordance with a further feature of the invention, there is provided an assembly for prevention of urinary incontinence in humans, the assembly including an applicator for positioning a foam or elastomer body in a urethra of a female or male. The applicator comprises a support portion for retaining the foam or elastomer body, the support portion comprising a tubular shell open at a first end and having a closed second end expandable in balloon-like fashion, and a manipulable portion comprising a plunger in part disposed in the shell open first end, the plunger being engageable with the foam or elastomer body at a first end of the plunger and having a head at a second end thereof. The assembly further includes the foam or elastomer body which comprises a body of foam or elastomer material disposed in the shell and removed from the shell closed end. The applicator plunger is moveable in the shell to force the foam or elastomer body through the shell into the shell closed second end to expand the shell second end in the afore-said balloon-like fashion.

In accordance with a still further feature of the invention, there is provided an assembly for prevention of urinary incontinence in humans, the assembly including an applicator for positioning a foam or elastomer body in a urethra of a female or male. The applicator comprises a support portion for retaining the foam or elastomer body, the support portion comprising an elongated projection, and a manipulable portion comprising a grip portion fixed to the projection. The assembly further includes the foam or elastomer body which comprises a discrete body of foam or elastomer material having a bore therein adapted to receive the applicator support portion projection, the foam or elastomer body being disposed on and extended over substantially the length of the projection. The projection is removable from the foam or elastomer body to disengage the foam or elastomer body from the applicator.

In accordance with a still further feature of the invention, there is provided a method for preventing an unwanted discharge of urine, comprising the steps of providing an applicator with an expandable body fixed thereto in a non-expanded condition, manipulating the applicator to insert the body into a urethra and to separate the applicator from the body, to permit the body to expand in the urethra, and drawing the body in expanded condition from the urethra by pulling an appendage extending from the body and exteriorly of the urethra, when discharge of urine is desired.

The above and other features of the invention, including various novel details of construction and combinations of parts, will now be more particularly described with reference to the accompanying drawings and pointed out in the claims. It will be understood that the particular devices and methods embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention from which its novel features and advantages will be apparent.

In the drawings.

DESCRIPTION OF THE PREFERRED EMBODIMENTS

Figure 1:
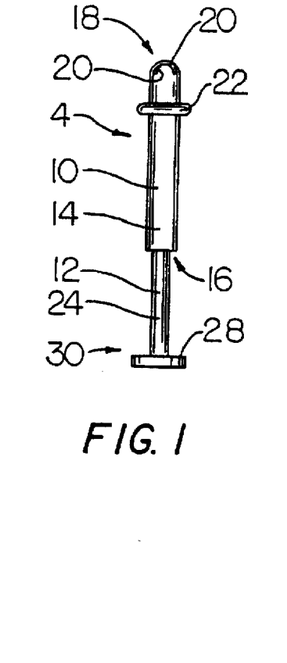
FIG. 1 is an elevational view of one form of assembly illustrative of an embodiment of the invention.
Figure 2:
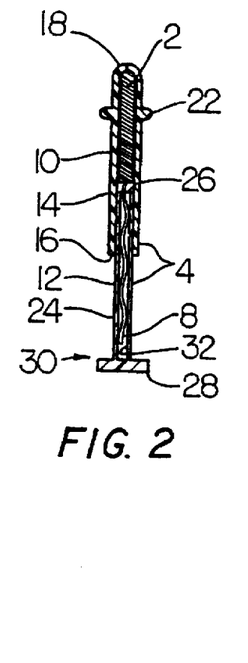
FIG. 2 is a sectional view of the assembly of FIG. 1.

Referring to FIGS. 1 and 2, it will be seen that an illustrative embodiment of the invention includes a foam or elastomer body 2 and an applicator 4 for positioning and depositing the foam or elastomer body 2 in the urethra of a human.

Figure 3:
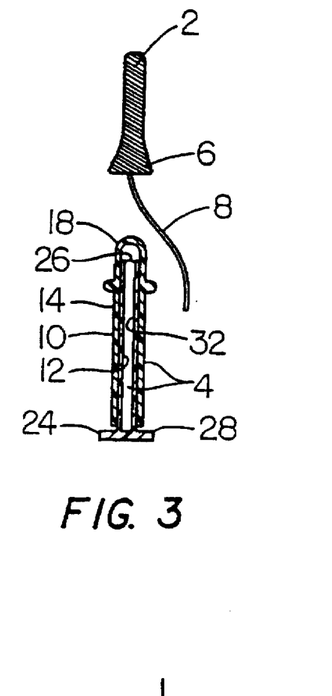
FIG. 3 is an exploded sectional view, showing a foam or elastomer body portion separated from the applicator portion of the assembly of FIGS. 1 and 2.

The foam or elastomer body 2 comprises a body of foam or elastomer material, such as closed or open cell polyurethane, polyethylene, latex, silicone, Kraton, foamed Kraton, cellulose, and the like, which is expandable upon release from a confined area. While the body 2 may be of any of such materials, it will be referred to hereinafter as "elastomer body". The elastomer body 2 is provided with an enlarged base portion 6 (FIG. 3). An appendage, such as a string 8, is fixed to the elastomer body base portion 6 and extends therefrom. The appendage may, alternatively, be a tab or extension (not shown) of the elastomer body 2.

The applicator 4 includes a support portion 10 for supporting the elastomer body 2 prior to use, and a manipulable portion 12 for moving the elastomer body 2 from its supported position to an operative position within the urethra.

The support portion 10 comprises a tubular shell 14 open at a first end 16 and having a second end 18 substantially closed but adapted to open in response to pressure thereupon internally of said shell. As shown in FIG. 1, the shell second end 18 may be formed as a closed end and provided with slits 20 which permit the shell second end 18 to open when the elastomer body 2 is pressed thereagainst, as will be further described herein below. The shell 14 is adapted to retain the elastomer body 2, as may be seen in FIG. 2. The shell 14 is provided with a collar 22 extending radially outwardly from the shell proximate, but removed from, the shell second end 18.

The manipulable portion 12 comprises a plunger 24 in part disposed in the shell open first end 16. The plunger 24 is engageable with the elastomer body 2 at a first end 26 of the plunger. The plunger 24 is provided with a head 28 at a second end 30 thereof. The plunger first end 26 is open and in communication with a chamber 32 for releasably retaining the string 8.

Figure 5:
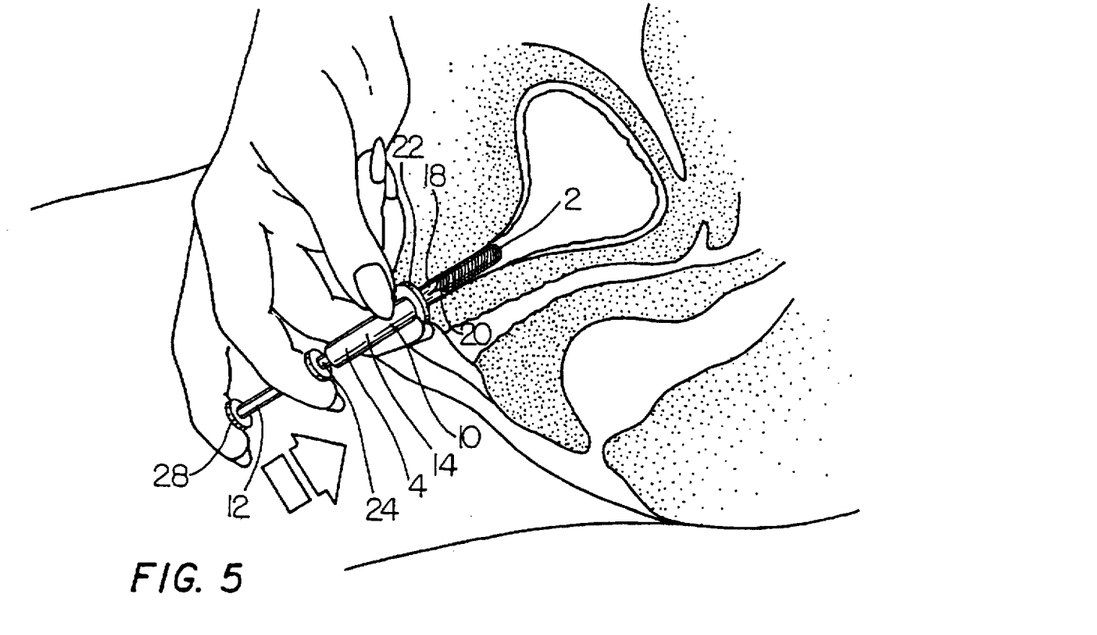
FIG. 5 is a diagrammatic illustration of the insertion of the foam or elastomer body of FIGS. 1–3 in the female urethra.

The applicator plunger 12 is moveable in the shell 14, as by operator hand pressure on the plunger head 28, to force the elastomer body 2 through the shell second end 18 (FIG. 5), to disengage the elastomer body 2 from the shell, as shown in FIG. 3.

Figure 4:
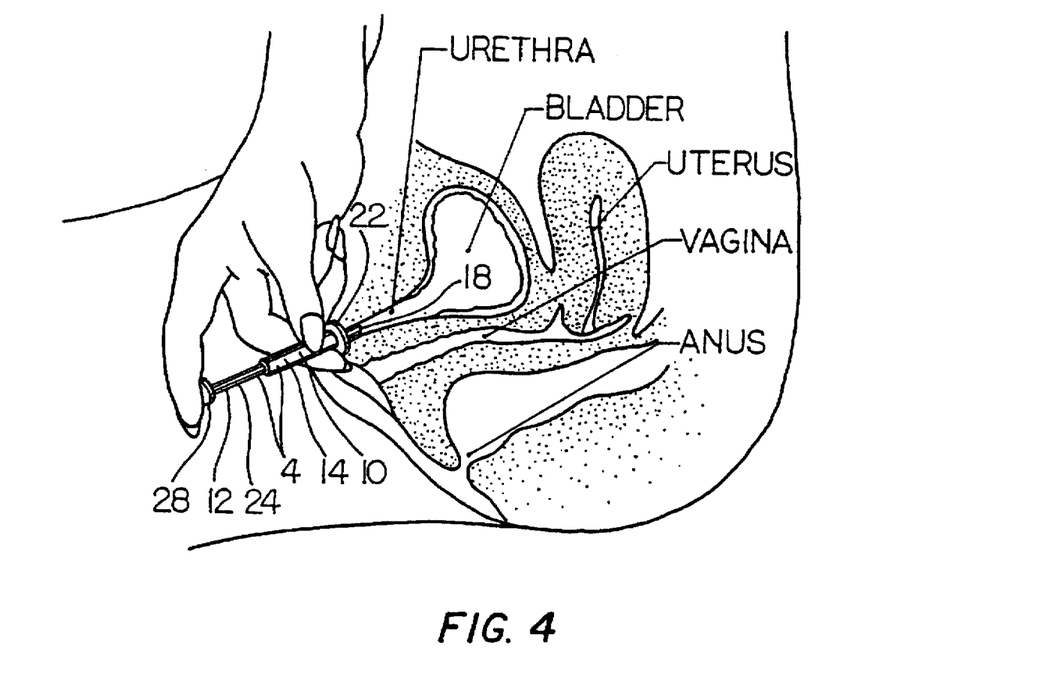
FIG. 4 is a diagrammatic illustration of the positioning of the assembly of FIGS. 1–3 for insertion of the foam or elastomer body in a female urethra.
Figure 6:
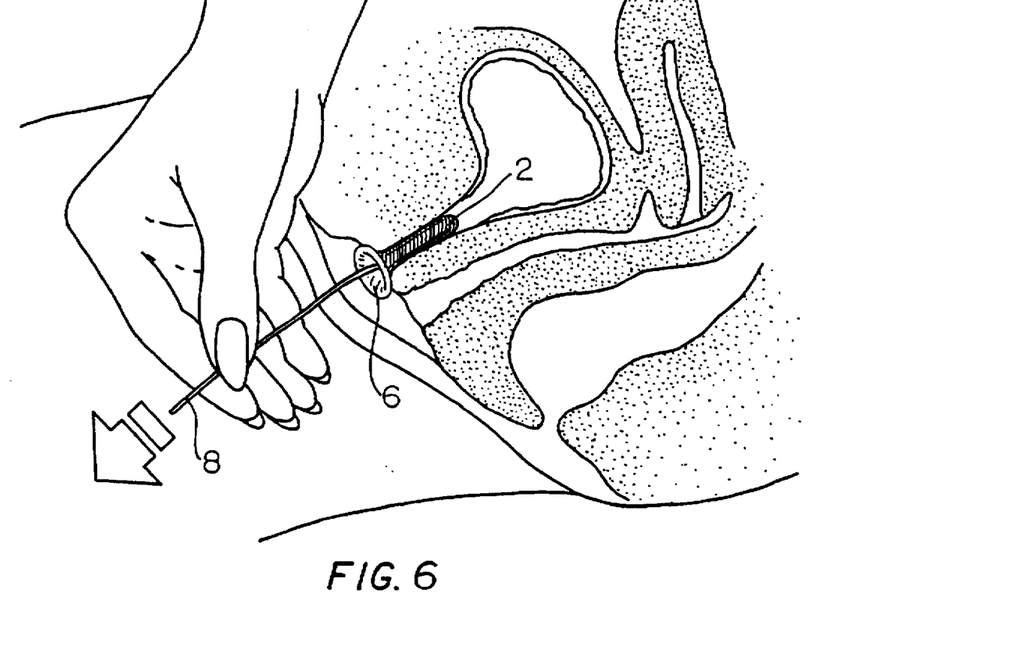
FIG. 6 is a diagrammatic illustration of the removal of the foam or elastomer body of FIG. 5 from the urethra.
Figure 7:
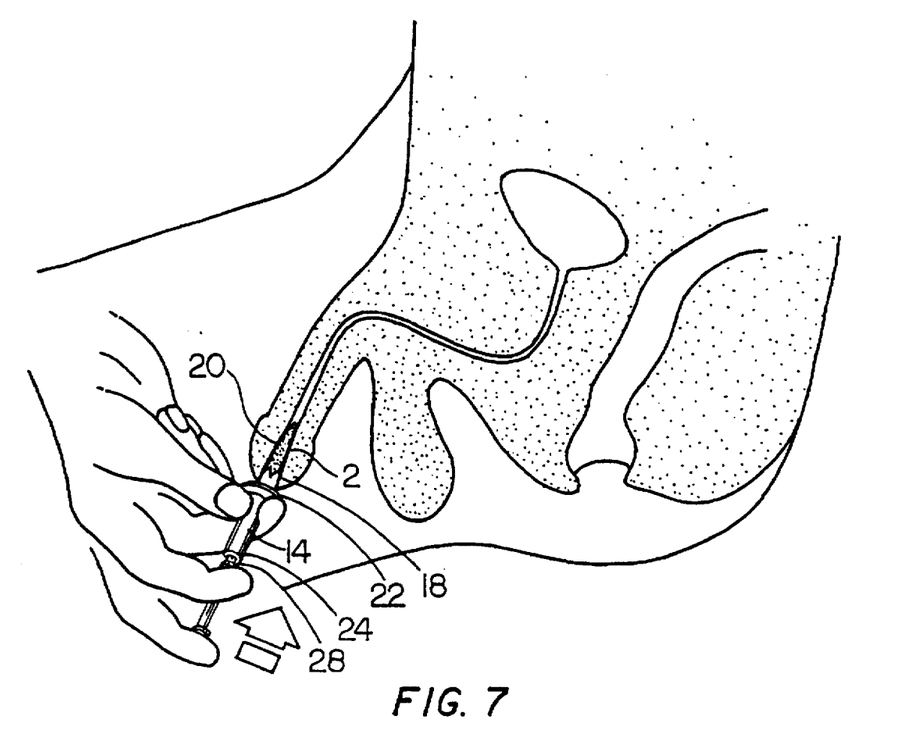
FIG. 7 is similar to FIG. 5, but illustrates insertion of the body of FIGS. 1–3 in the urethra of a male.

In use (FIGS. 4 and 7), the operator grasps the applicator shell 14, and inserts the shell second end 18 in the urethra. The collar 22 of the shell 14 prevents excessive entry of the device into the urethra (FIGS. 4 and 7). The operator places a finger on the plunger head 28 and presses the plunger 24 into the shell 14 (FIGS. 5 and 7) to move the elastomer body 2. The pressure of the elastomer body 2 against the second end 18 of the shell forces open the slits 20 in the second end 18 to permit egress of the elastomer body, which thereupon expands to fill the urethra. Upon removal of the applicator 4 from the urethra, the elastomer body 2 remains in operative position in the urethra (FIG. 6). The expanded base portion 6 of the elastomer body 2 serves as a meatal plate and prevents movement of the elastomer body towards the bladder.

When it is desired to remove the elastomer body 2 from the urethra, the operator grasps the string 8 (FIG. 6) and pulls the elastomer body therefrom. Both the applicator 4 and the elastomer body 2 may be disposed of through ordinary trash disposal means.

Figure 8:
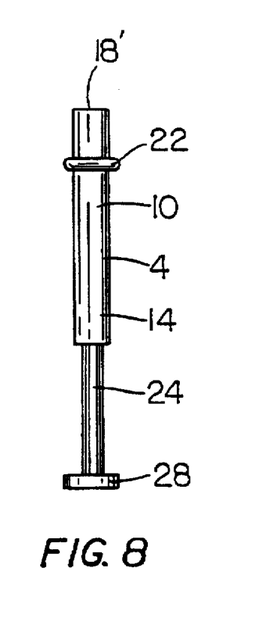
FIG. 8 is an elevational view, similar to FIG. 1, of another form of assembly illustrative of an alternative embodiment of the invention.
Figure 9:
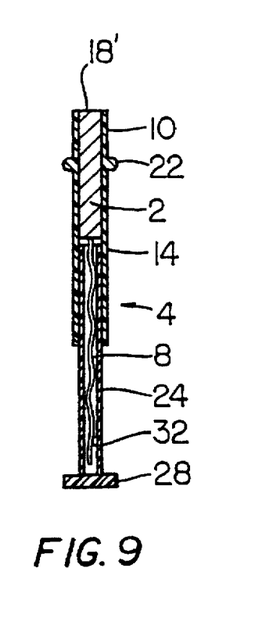
FIG. 9 is a sectional view, similar to FIG. 2, of the embodiment shown in FIG. 8.

Referring to FIGS. 8 and 9, it will be seen that an alternative embodiment of the assembly of FIGS. 1–3 includes an open second end 18'. Otherwise, the structure and operation of the embodiment shown in FIGS. 8 and 9 are substantially the same as the structure and operation of the embodiment shown in FIGS. 1–3.

Figure 10:
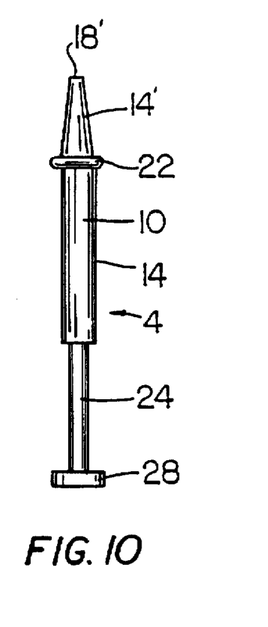
FIG. 10 is an elevational view of another form of assembly illustrative of an alternative embodiment of the invention.

In FIG. 10, there is shown an alternative embodiment of tubular shell 14 having a frusto-conically shaped nozzle portion 14' having the open end 18' at the small end thereof.

Figure 11:
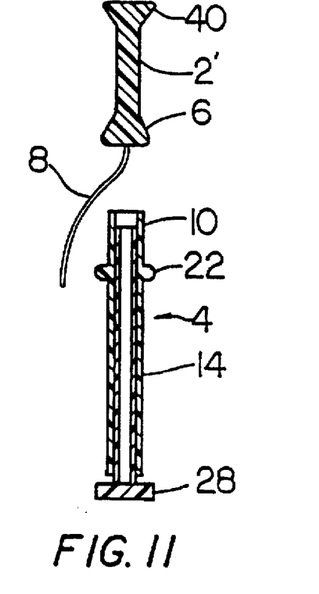
FIG. 11 is a sectional view, similar to that shown in FIG. 3, of an alternative embodiment of elastomer body.

In FIG. 11, there is shown an alternative embodiment of elastomer body 2' having an enlarged distal end 40. Otherwise, the structure and operation of the body 2' is substantially the same as the structure and operation of the body 2 shown in FIG. 3.

Figure 12:
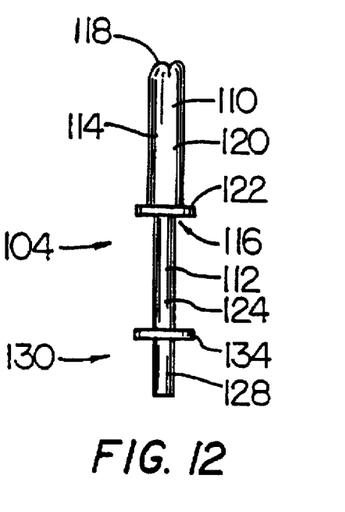
FIG. 12 is an elevational view of another form of assembly illustrative of an alternative embodiment of the invention.
Figure 13:
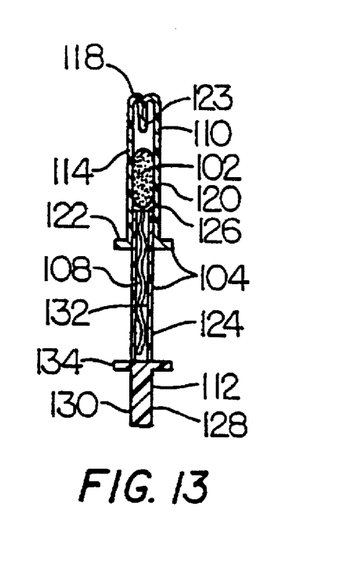
FIG. 13 is a sectional view of the assembly of FIG. 12.

Referring to FIGS. 12 and 13, it will be seen that another illustrative embodiment of the invention includes an elastomer body 102 and an applicator 104 for positioning and depositing the elastomer body in the urethra.

Figure 14:
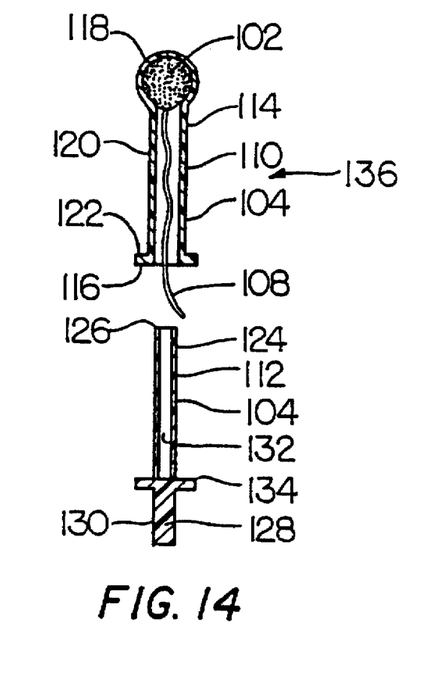
FIG. 14 is an exploded sectional view of the assembly of FIGS. 12 and 13, showing a foam or elastomer body portion moved to an operative position.

The elastomer body 102 comprises a mass of foam or elastomer material which is readily compressible upon application of pressure thereto and is expandable upon release of pressure, or release from a confined space. Suitable materials have been found to be the afore-mentioned polyurethane, polyethylene, latex, silicone, Kraton, foamed Kraton, cellulose, and the like. The elastomer body 102 has fixed thereto and extending therefrom an appendage, such as string 108 (FIGS. 13 and 14).

The applicator 104 includes a support portion 110 for supporting the elastomer body 102 prior to use, and during use, and a manipulable portion 112 for moving the body 102 to an operative position.

Figure 19:
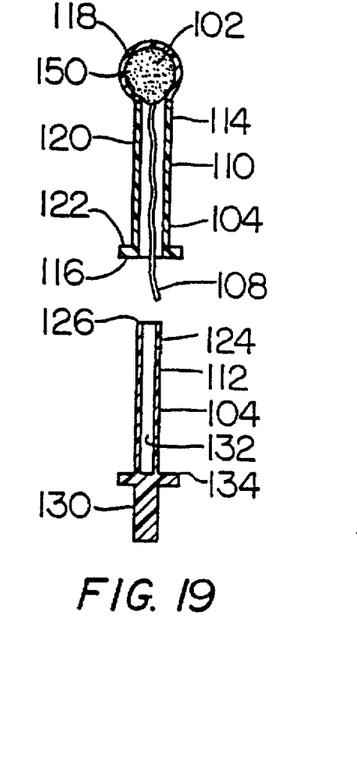
FIG. 19 is an exploded sectional view, similar to FIG. 14, but showing an alternative embodiment.

The support portion 110 comprises a tubular shell 114 open at a first end 116 thereof and having a second end 118 closed and expandable in balloon-like fashion (FIG. 14) in response to pressure thereupon internally of the shell. The shell 114 is adapted to support and retain the elastomer body 102 prior to use, as may be seen in FIG. 8. The shell 114 is provided with a collar 122 extending radially outwardly from the shell at the shell second end 118. The shell preferably is of a thermoplastic elastomeric, or semi-rigid foam, material, which is sufficiently rigid to support the body 102 in a barrel portion 120 of the shell 114, but sufficiently expandable to permit the required expansion at the second end 118 thereof. To facilitate expansion, the second end 118 of the shell 114 may be provided with folds 123 (FIG. 13) disposed internally of the shell. Alternatively, the second end 118 may be a discrete end component 150 (FIG. 19) of a second material attached to the tubular shell 114. The second material may be provided with physical properties to permit the required expansion.

The manipulable portion 112 comprises a plunger 124 in part disposed in the shell open first end 116. The plunger 124 is engageable with the body 102 at a first end 126 of the plunger. The plunger 124 is provided with a head 128 at a second end 130 thereof. The plunger first end 126 is open and in communication with a chamber 132 for releasably retaining the string 108.

The applicator plunger 124 is moveable in the shell 114, as by operator hand pressure on the plunger head 128, to force the body 102 through the shell barrel portion 120 into the shell expandable second end 118. Continued movement of the plunger 124 compresses the body 102 axially, while release of the body from the barrel portion 120, in combination with the axial compression of the body, causes radial expansion of the body 102 to expand the shell second end 118 balloon-like, as shown in FIG. 9, so as to obstruct the urethra and/or bladder neck. Axial movement of the plunger 124 in the shell 114 is limited by a stop ring 134 engageable with the shell collar 122.

Figure 15:
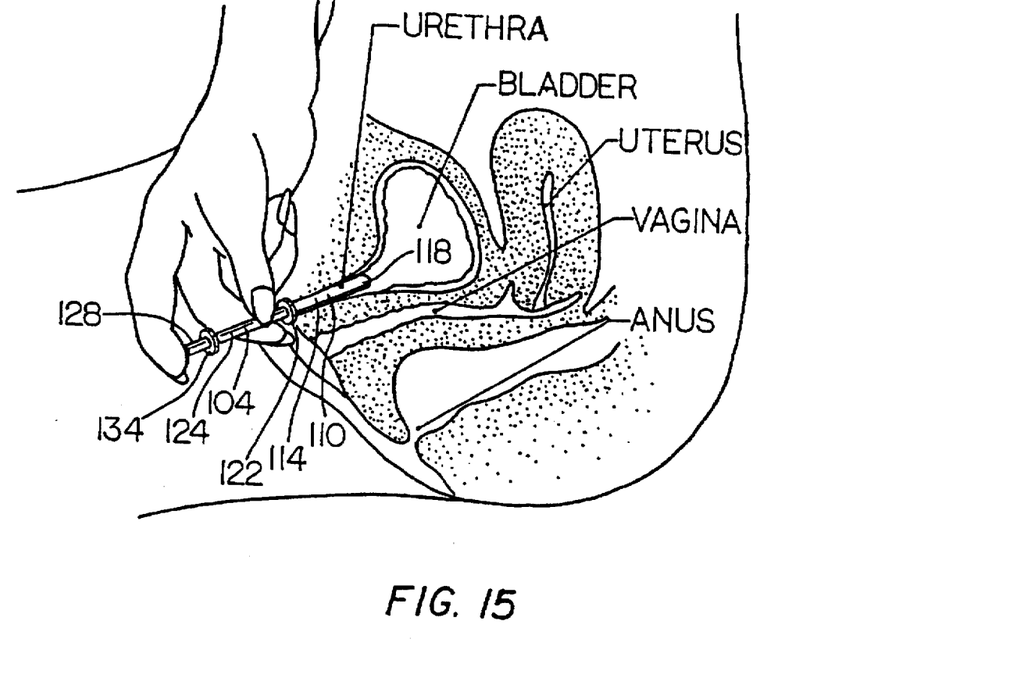
FIGS. 15–17 are diagrammatic illustrations of, respectively, the positioning of the assembly of FIGS. 12 and 13, the placement of a portion of the assembly in the urethra, and removal of that portion of the assembly from the urethra of a female.
Figure 16:
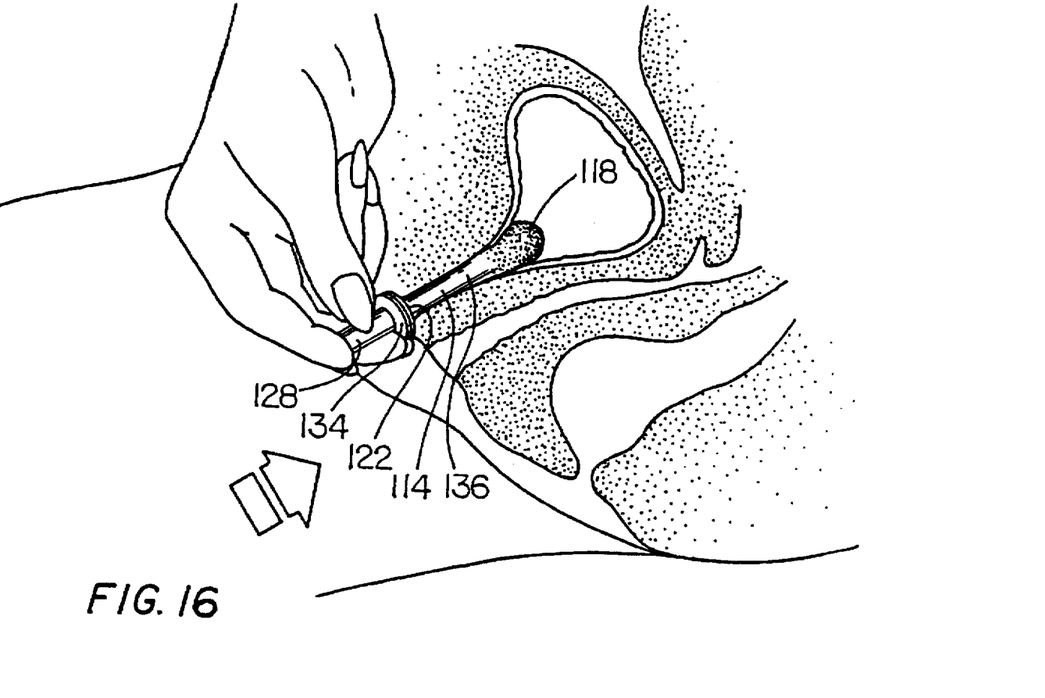
Figure 18:
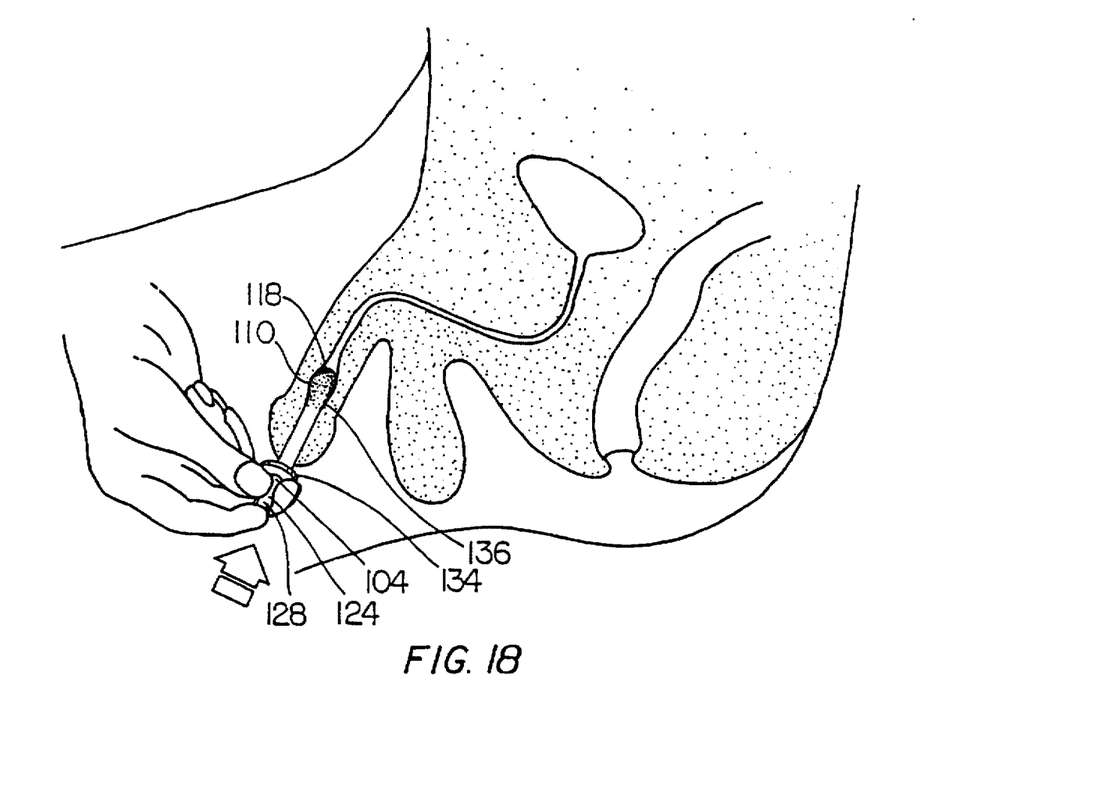
FIG. 18 is similar to FIG. 16, but shows placement and operation of the embodiment of FIGS. 12–14 in the urethra of a male.

In use (FIGS. 15 and 18), the operator grasps the applicator plunger 124 and inserts the shell second end 118 into the urethra. The collar 122 of the shell 114 prevents excessive entry of the device into the urethra. The operator places a finger on the plunger head 128 and presses the plunger 124 into the shell 114 until the plunger stop ring 134 engages the shell collar 122 (FIG. 16). The pressure of the foam body 102 against the second end 118 of the shell 114 forces the shell folds 123 to fill and expand to a ball-like configuration and obstruct the urethra. The plunger 124 is then withdrawn from the shell 114 to leave the shell and foam body 102 in the urethra. At this point, the shell 114 ceases being, in function, an applicator, and becomes in combination with the foam body, a urethral plug 136 disposed in the urethra. The shell collar 122 serves as a meatal plate and prevents movement of the plug 136 into the bladder.

Figure 17:
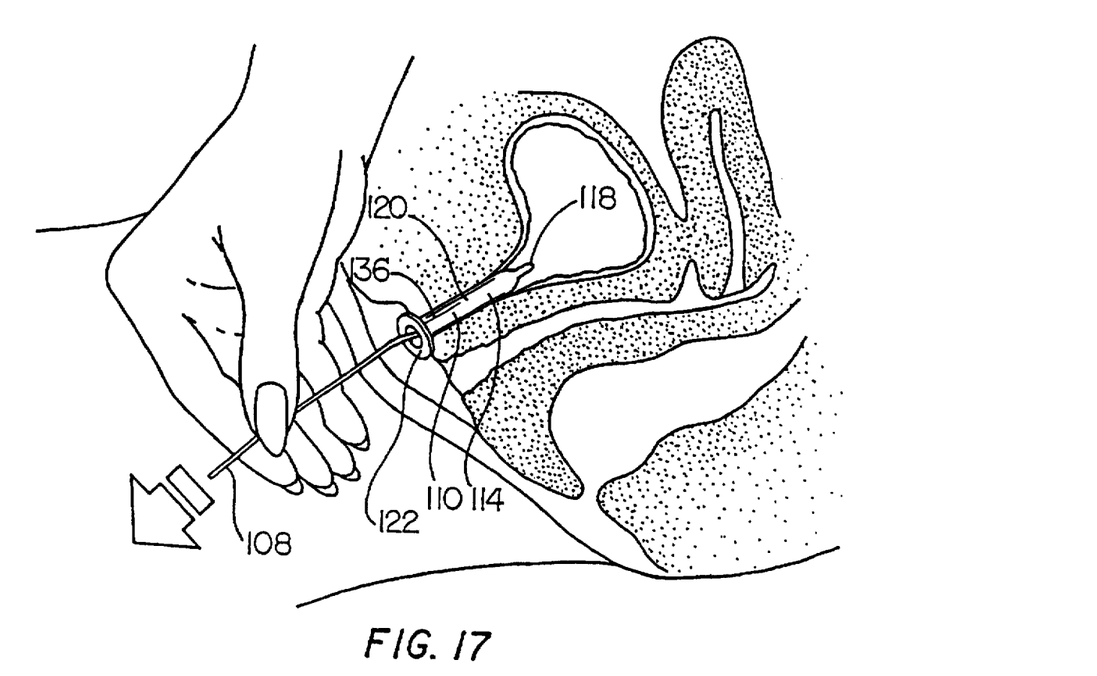

To remove the urethral plug 136 from the urethra, the operator pulls on the string 108 (FIG. 17) which moves the foam body from the shell second end 118 into the shell barrel portion 120, whereupon the shell second end 118 collapses to permit withdrawal of the plug 136 from the urethra.

All components of the alternative embodiment may be disposed of as ordinary trash.

Figure 20:
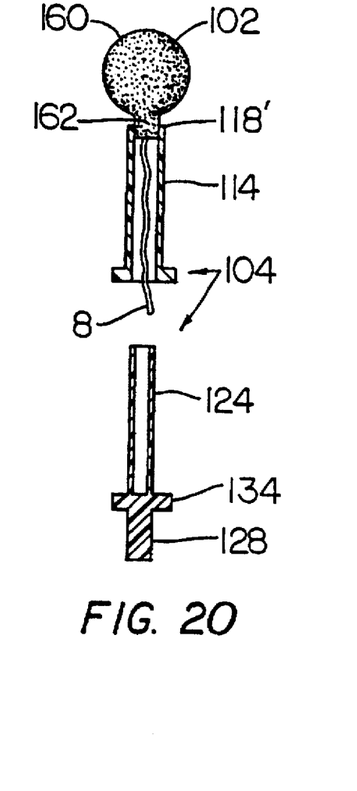
FIG. 20 is an exploded sectional view, similar to that shown in FIG. 14, of an alternative embodiment of applicator support portion.

In FIG. 20, there is shown an alternative embodiment in which the second end 118' of the tubular shell 114 is open and the elastomer body 102 is incompletely expelled from the shell, such that a major portion 160 of the elastomer body 102 is pushed out of the open end 118' of the shell 114 and expands to fill the urethra, while a minor portion 162 of the body 102 remains in the shell 114. As in the embodiment illustrated in FIGS. 12–14, the body 102 and shell 114, once in operative position, act in cooperation with each other as a urethral plug. Pulling on the string 8 removes the plug 102, 114 from the urethra.

Figure 21:
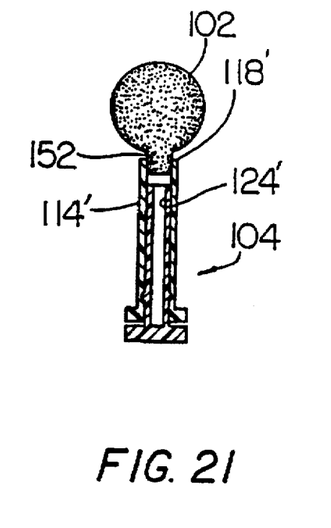
FIG. 21 is a sectional view of an alternative embodiment of assembly, similar to that shown in FIG. 20.
Figure 22:
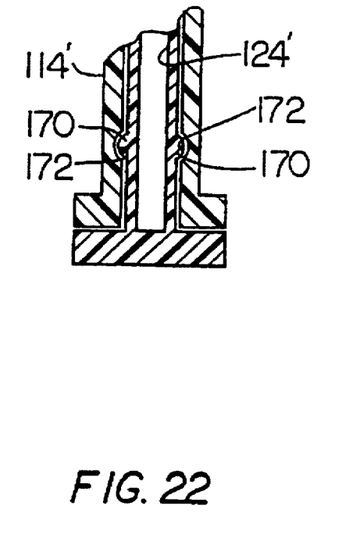
FIG. 22 is an enlarged sectional view of a portion of the assembly of FIG. 21.

In FIG. 21, there is shown a further alternative embodiment, similar to that shown in FIG. 20, but in which the plunger 124' is locked in the shell 114' with the elastomer body 102 held in the second end 118' of the shell 114' and expanded in the balloon-like fashion, and in part exposed through an opening 152 in the shell second end 118'. In this embodiment, the entire assembly becomes a urethral plug, as shown in FIG. 21. To facilitate locking of the plunger 124' in the shell 114', the plunger and shell may be provided with cooperating detents 170 and recesses 172 (FIG. 22) which interlock in a snap-fit manner to secure the plunger 124' and shell 114' together.

Figure 23:
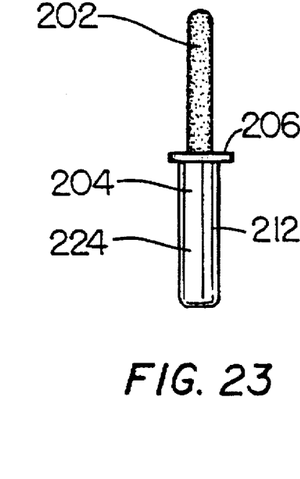
FIG. 23 is an elevational view of another form of assembly illustrative of another alternative embodiment of the invention.
Figure 24:
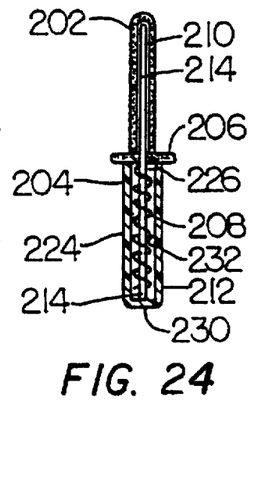
FIG. 24 is a sectional view of the assembly of FIG. 23.
Figure 25:
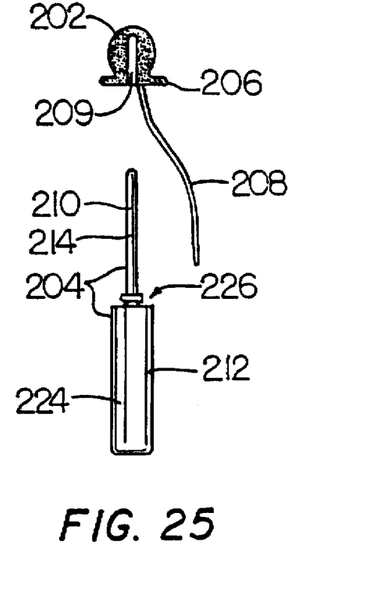
FIG. 25 is an exploded view of the assembly of FIGS. 23 and 24, showing a foam or elastomer body portion in section separated from an applicator portion, shown in elevation.
Figure 26:
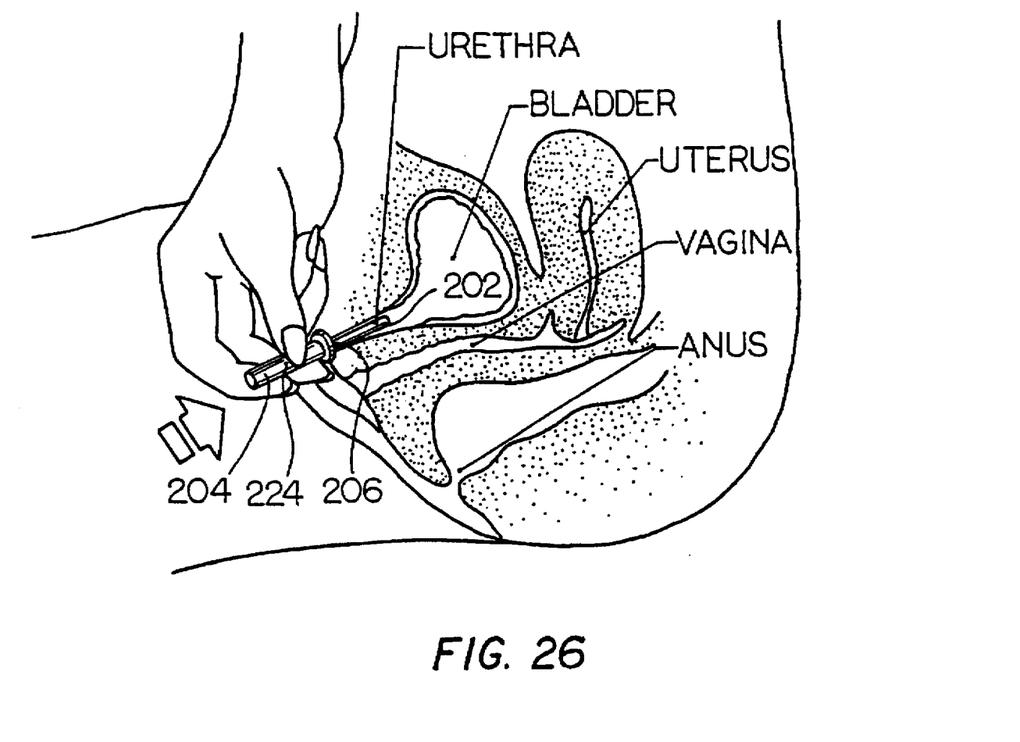
FIGS. 26–28 are diagrammatic illustrations of, respectively, the positioning of the assembly in a female urethra, the placement of the foam or elastomer body in the urethra, and the removal of the foam body from the urethra.

Referring to FIGS. 23 through 29, it will be seen that still another illustrative embodiment of the invention includes an elastomer body 202 and an applicator 204 for positioning and depositing the body in the urethra. The elastomer body 202 may be configured in a relaxed or first shape (FIGS. 25, 27–29), and in an elongated or second shape (FIGS. 23, 24, 26). The elastomer body 202 comprises a body of foam or elastomer material, such as polyurethane, polyethylene, latex, silicone, Kraton, foamed Kraton, cellulose, and the like, which is expandable and which may be stretched over an elongated support to achieve an elongated or second shape (FIG. 24). The body 202 is provided with an enlarged portion at one end and an expanded base portion 206. An appendage, such as a string 208, is fixed to the body base portion 206 and extends therefrom. The body 202 is further provided with a central bore 209 therein (FIG. 25).

The applicator 204 includes a support portion 210 for supporting the elastomer body 202 prior to use, and a manipulable portion 212 for moving the body 202 into operative position within the urethra.

The support portion 210 comprises an elongated projection 214 for disposition in the elastomer body central bore 209, and the manipulable portion 212 comprises a grip portion 224 fixed to the projection 214. The grip portion 224 is open at a first end 226 thereof and is provided with a chamber 232 (FIG. 24) in communication with the open end 226 for releasably retaining the string 208.

As shown in FIG. 24, the projection 214 may extend from a closed second end 230 of the grip portion 224, centrally thereof, and through the open first end 226, with the string 208 coiled around the projection 214 or otherwise disposed in the grip portion chamber 232.

Figure 27:
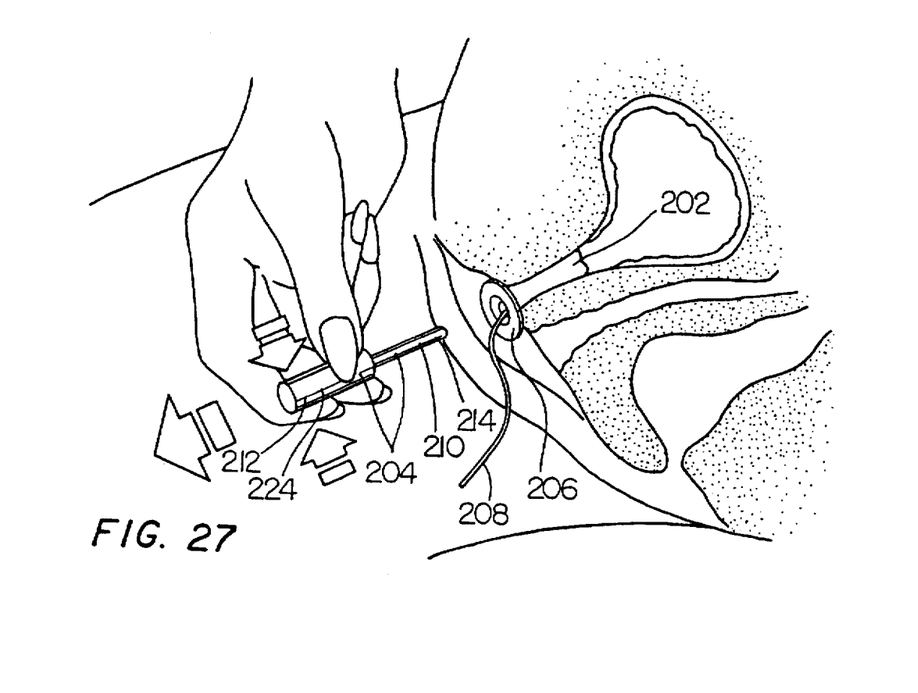
Figure 28:
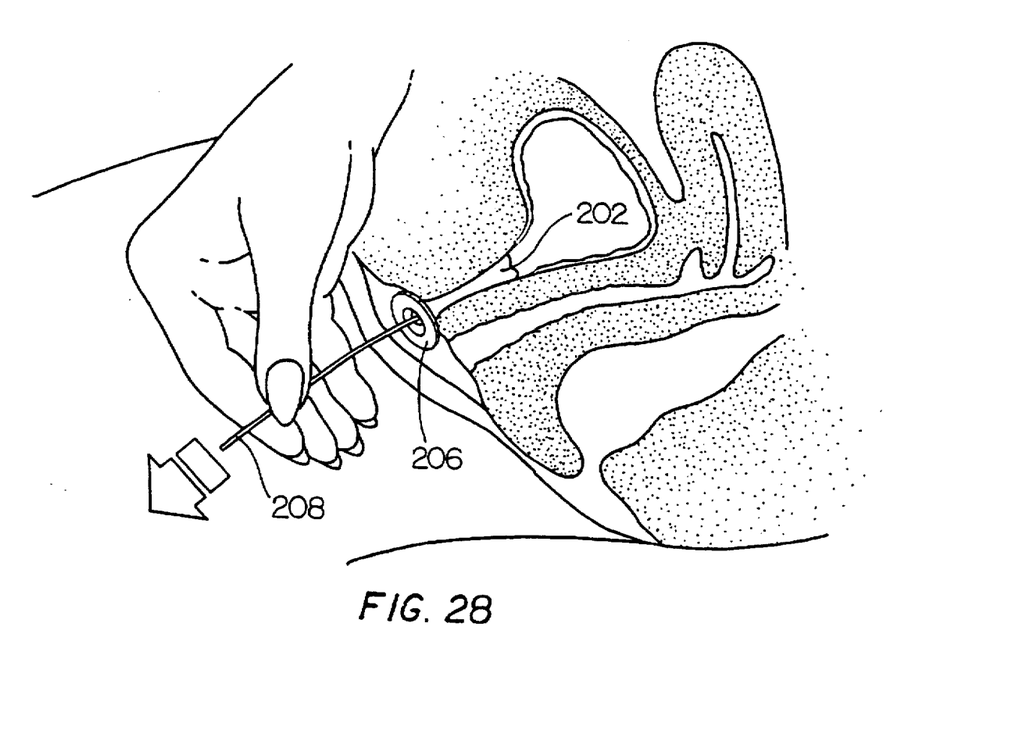
Figure 29:
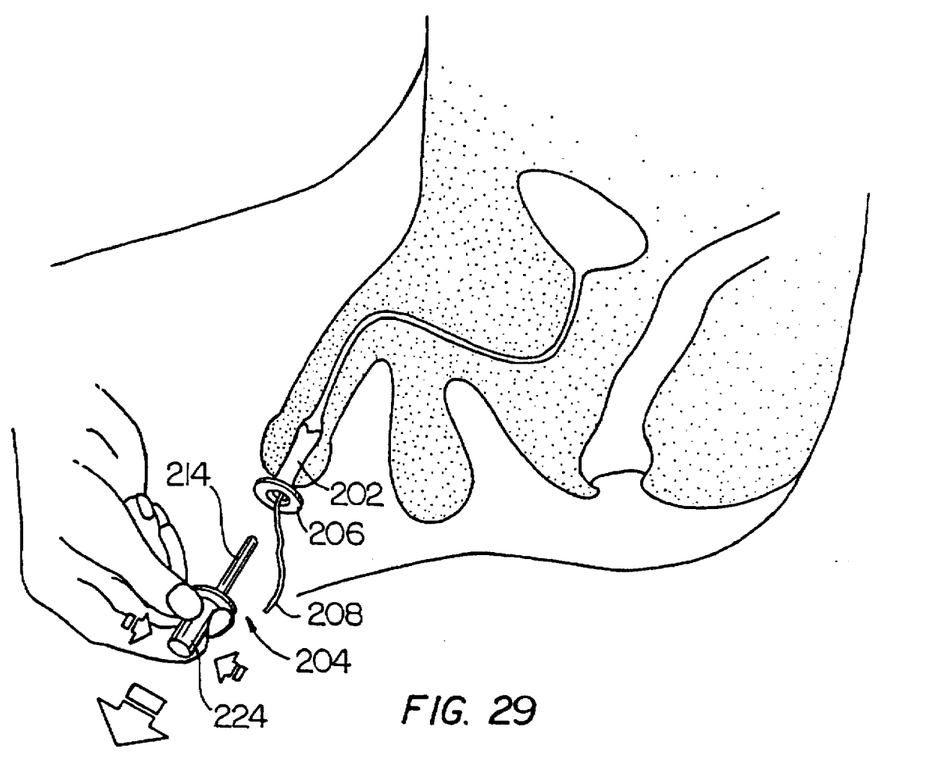
FIG. 29 is a diagrammatic illustration of the insertion of the foam or elastomeric body of FIGS. 23–25 in a male urethra.

In use (FIG. 26), the operator grasps the applicator grip portion 224 and inserts the projection 214, with the elastomer body 202 extended thereover (FIG. 24), into the urethra. The elastomer body expanded base portion 206 prevents excessive entry of the device into the urethra (FIG. 26). The operator actuates the grip portion 224 of the applicator 204 (FIGS. 27 and 29) to remove the applicator from the foam body 202, leaving the foam body in its expanded condition in the urethra. As illustrated in FIGS. 27–29, the body 202 thus returns to its relaxed, first shape in the urethra. Such actuation may be by rotating, squeezing or pulling the grip portion 224. As the applicator 204 disengages from the body 202, the string 208 disengages from the applicator. The expanded base portion 206 of the body 202 serves as a meatal plate and prevents migration of the body into the bladder.

When it is desired to remove the body 202 from the urethra, the operator merely grasps the string 208 and pulls the body from the urethra (FIG. 28).

As in the case of the other embodiments, the components of this alternative embodiment may be disposed of through normal trash disposal means.

Thus, there are presented alternative embodiments of assemblies for preventing urinary incontinence in females and males. The assemblies presented herein prevent loss of urine which can occur during physical exertion, sometimes as little as laughing, coughing, sneezing, or the like. It is intended that the applicator and elastomer body assembly be sterile and individually wrapped, with several assemblies packaged in a box.

It is to be understood that the present invention is by no means limited to the particular constructions herein disclosed and/or shown in the drawings, but also comprises any modifications or equivalents within the scope of the claims.

Having thus described our invention, what we claim as new and desire to secure by Letters Patent of the United States is:

1. A method for controlling unwanted discharge of urine, comprising the steps of:
   providing an applicator including an expandable body fixed thereto in a non-expanded condition;
   manipulating said applicator to insert said body into a urethra and to separate said applicator from said body, to permit said body to expand in the urethra; and
   withdrawing said body in its expanded condition from the urethra by pulling an appendage extending from said body and exteriorly of the urethra when discharge of urine is desired.

2. The method in accordance with claim 1 wherein said applicator comprises a shell and a plunger, with said body disposed in said shell, and said manipulation of said applicator to insert said body in the urethra comprises positioning an end of said shell in the urethra and moving said plunger in said shell to expel said body from said shell and into the urethra, and said manipulation of said applicator to separate said applicator from said body comprises withdrawal of said applicator from the urethra.

3. The method in accordance with claim 1 wherein said applicator comprises a plunger, and said body comprises an expandable mass disposed in a shell having an expandable end, and said manipulation of said applicator to insert said body in the urethra comprises positioning said plunger to move said shell into the urethra and moving said plunger in said shell to move said mass in said shell to said expandable end of said shell to permit expansion of said mass and said shell expandable end, and said manipulation of said applicator to separate said applicator from said body comprises withdrawal of said plunger from said shell.

4. The method in accordance with claim 1 wherein said applicator comprises a plunger, and said body comprises an expandable mass disposed in a shell having an open end, and said manipulation of said applicator to insert said body in the urethra comprises positioning said plunger to move said shell into the urethra and moving said plunger in said shell to move said mass in said shell to a position in which a portion of said mass extends beyond said shell open end to permit expansion of said portion of said mass, and said manipulation of said applicator to separate said applicator from said body comprises withdrawal of said plunger from said shell.

5. The method in accordance with claim 1 wherein said applicator comprises a grip portion and an elongated projection extending from said grip portion with said expandable body being stretched over said elongated projection, and said manipulation of said applicator to insert said body into the urethra comprises positioning said body in the urethra by manipulation of said grip portion of said applicator, and said manipulation of said applicator to separate said applicator from said body comprises withdrawal of said elongated projection from said body, to permit said body to expand in the urethra.

6. A method for controlling urinary incontinence in humans, comprising the steps of:

providing an applicator including an occlusion body fixed thereto, said occlusion body being configured in a first shape;

manipulating said applicator to stretch said body over said applicator, such that said body is reconfigured into a second shape;

inserting said body into the urethra, bladder neck or bladder;

separating said applicator from said body to permit said body to return to said first shape in the urethra; and removing said body in said first shape from the urethra.

7. The method in accordance with claim 6 wherein the separating step further comprises one of rotating, squeezing, pushing and pulling at least a portion of said applicator.

8. The method in accordance with claim 6 wherein the removing step further comprises pulling an appendage extending from said body and exteriorly of the urethra when discharge of urine is desired.

9. The method in accordance with claim 6 wherein said applicator being provided comprises a grip portion and an elongated projection extending from said grip portion with said occlusion body being disposed on said elongated projection, said manipulation of said applicator to insert said body into the urethra and stretch said body over said projection, comprises positioning said body in the urethra by manipulation of said grip portion of said applicator, and said manipulation of said applicator to separate said applicator from said body comprises withdrawal of said elongated projection from said body, to permit said body to assume said first shape in the urethra.

10. A method for controlling urinary incontinence in humans, comprising the steps of:

providing an applicator including an occlusion body fixed thereto, said occlusion body being configured in an elongated shape;

inserting said elongated body into the urethra, bladder neck or bladder;

separating said applicator from said body to permit said body to return to a relaxed shape; and removing said body in said relaxed shape from the urethra.

11. The method in accordance with claim 10 wherein the separating step further comprises actuating at least a portion of said applicator by one of rotating, squeezing, pushing and pulling.

12. The method in accordance with claim 10 wherein the removing step further comprises pulling an appendage extending from said body and exteriorly of the urethra when discharge of urine is desired.

13. The method in accordance with claim 10 wherein said applicator being provided comprises a grip portion and an elongated projection extending from said grip portion with said occlusion body being stretched over said elongated projection, said manipulation of said applicator to insert said body into the urethra comprises positioning said body in the urethra by manipulation of said grip portion of said applicator, and said manipulation of said applicator to separate said applicator from said body comprises withdrawal of said elongated projection from said body, to permit said body to assume the relaxed shape in the urethra.

* * * * *